(12) United States Patent
Hu et al.

(10) Patent No.: US 11,484,697 B2
(45) Date of Patent: Nov. 1, 2022

(54) PINCH CLAMP

(71) Applicant: Becton, Dickinson and Company, Franklin Lakes, NJ (US)

(72) Inventors: Olivia Hu, Shanghai (CN); Ralph L. Sonderegger, Farmington, UT (US); Shaun Staley, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/307,681

(22) Filed: May 4, 2021

(65) Prior Publication Data

US 2021/0260357 A1     Aug. 26, 2021

Related U.S. Application Data

(63) Continuation of application No. 16/573,709, filed on Sep. 17, 2019, now Pat. No. 11,020,581.

(60) Provisional application No. 62/741,382, filed on Oct. 4, 2018.

(51) Int. Cl.
*A61M 39/28* (2006.01)
*F16K 7/06* (2006.01)

(52) U.S. Cl.
CPC ......... *A61M 39/284* (2013.01); *F16K 7/063* (2013.01); *A61M 39/287* (2013.01); *F16K 7/066* (2013.01)

(58) Field of Classification Search
CPC ...... F16K 7/063; F16K 7/066; A61M 39/284; A61M 39/287
See application file for complete search history.

(56) References Cited

U.S. PATENT DOCUMENTS

| 4,346,869 A | ‡ | 8/1982 | MacNeill | A61M 39/284 |
| | | | | 251/10 |
| 4,589,626 A | ‡ | 5/1986 | Kurtz | A61M 39/288 |
| | | | | 251/10 |
| 8,328,763 B2 | ‡ | 12/2012 | Traversaz | A61M 39/281 |
| | | | | 604/167.01 |
| 9,050,447 B2 | ‡ | 6/2015 | Davis | A61M 39/28 |
| 9,872,978 B1 | ‡ | 1/2018 | Zaborsky | A61L 2/08 |
| 10,322,278 B2 | ‡ | 6/2019 | Kato | A61M 39/284 |
| 10,398,836 B2 | ‡ | 9/2019 | Kato | A61M 39/284 |
| 10,512,768 B2 | ‡ | 12/2019 | Tsukamoto | A61M 39/28 |
| 2010/0152681 A1 | ‡ | 6/2010 | Mathias | F16K 7/063 |
| | | | | 604/250 |

(Continued)

FOREIGN PATENT DOCUMENTS

| CN | 103391792 B | | 11/2013 |
| WO | WO-2016/002487 | ‡ | 1/2016 |
| WO | WO-2017/074681 | ‡ | 5/2017 |

*Primary Examiner* — Umashankar Venkatesan
(74) *Attorney, Agent, or Firm* — Kirton McConkie; Whitney Blair; Kevin Stinger (57) ABSTRACT

Pinch clamps are provided which generate positive displacement while also preventing rebound. To prevent rebound while providing positive displacement, the upper and lower clamping surfaces may be configured to form a pinch profile along which the tubing is compressed with the pinch point being formed at the distal end of the pinch profile. To further prevent rebound, the lower arm of the pinch clamp can include blocking ribs that interface with the upper clamping surface to prevent distal travelling of the pinch point even if the upper arm is forced into an over-engaged position.

3 Claims, 9 Drawing Sheets

(56) References Cited

U.S. PATENT DOCUMENTS

| | | | |
|---|---|---|---|
| 2012/0035553 A1‡ | 2/2012 | Lombardo | A61M 39/284 604/250 |
| 2013/0310768 A1‡ | 11/2013 | Ebara | A61M 39/28 604/250 |
| 2014/0070122 A1* | 3/2014 | Imai | A61M 5/1407 29/890.12 |
| 2017/0009895 A1‡ | 1/2017 | Stanton | A61M 39/28 |
| 2017/0120040 A1 | 5/2017 | Burkholz et al. | |
| 2018/0104467 A1 | 4/2018 | Kato | |

\* cited by examiner
‡ imported from a related application

PINCH CLAMP

RELATED APPLICATIONS

This application is a continuation of U.S. application Ser. No. 16/573,709, filed Sep. 17, 2019, and entitled "PINCH CLAMP," which claims the benefit of U.S. Provisional Application No. 62/741,382, filed Oct. 4, 2018, and entitled "PINCH CLAMP," which are incorporated herein in their entirety.

BACKGROUND

Pinch clamps are commonly employed to obstruct tubing of an intravenous or other medical system. Pinch clamps oftentimes have a clam-shell design where an upper arm is connected to a lower arm via a living hinge. The lower arm is typically configured to retain the upper arm in a closed position in which the tubing is clamped between the two arms.

Traditional pinch clamp designs suffer from various drawbacks. For example, due to the molding process, pinch clamps typically have sharp edges that may cause patient discomfort. The molding process also causes the pinch clamps to be relatively bulky. Many pinch clamp designs also allow the two arms to move laterally when in the closed position leading to unintended disengagement of the pinch clamp. Even when lateral disengagement features are incorporated into these designs, asymmetry in the features oftentimes leads to failure in one direction.

Figure 1:
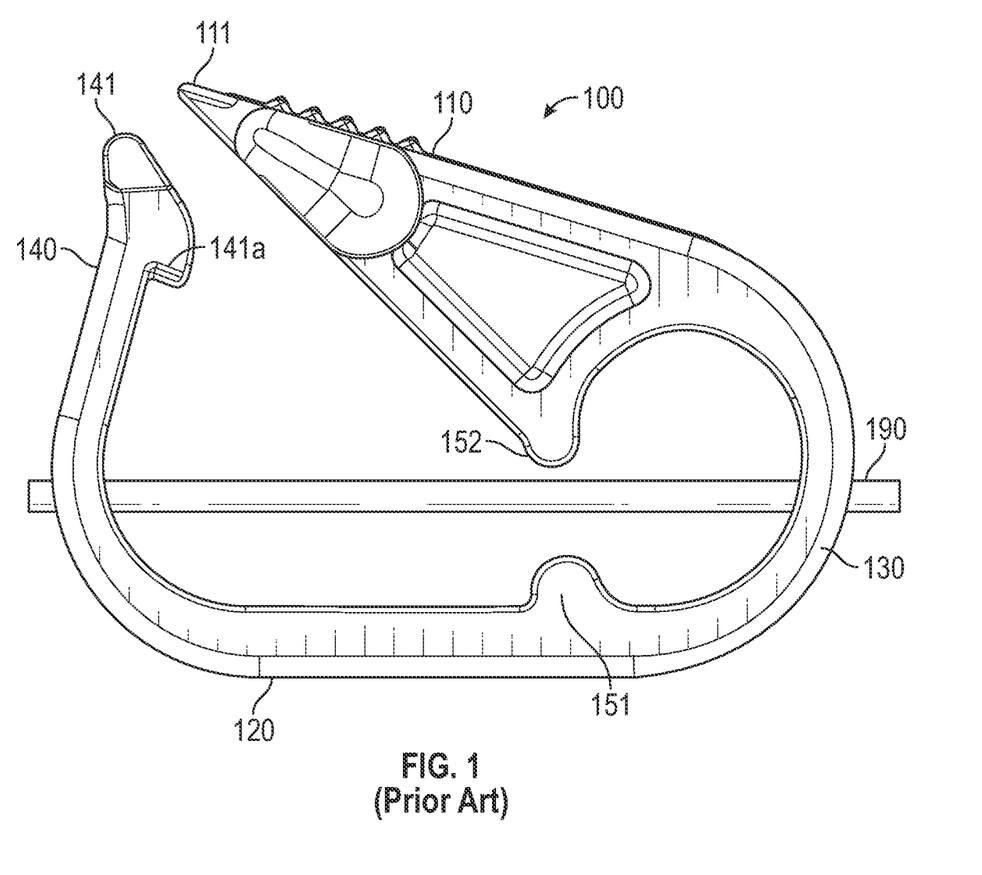
FIG. 1 illustrates a prior art pinch clamp.
Figure 1A:
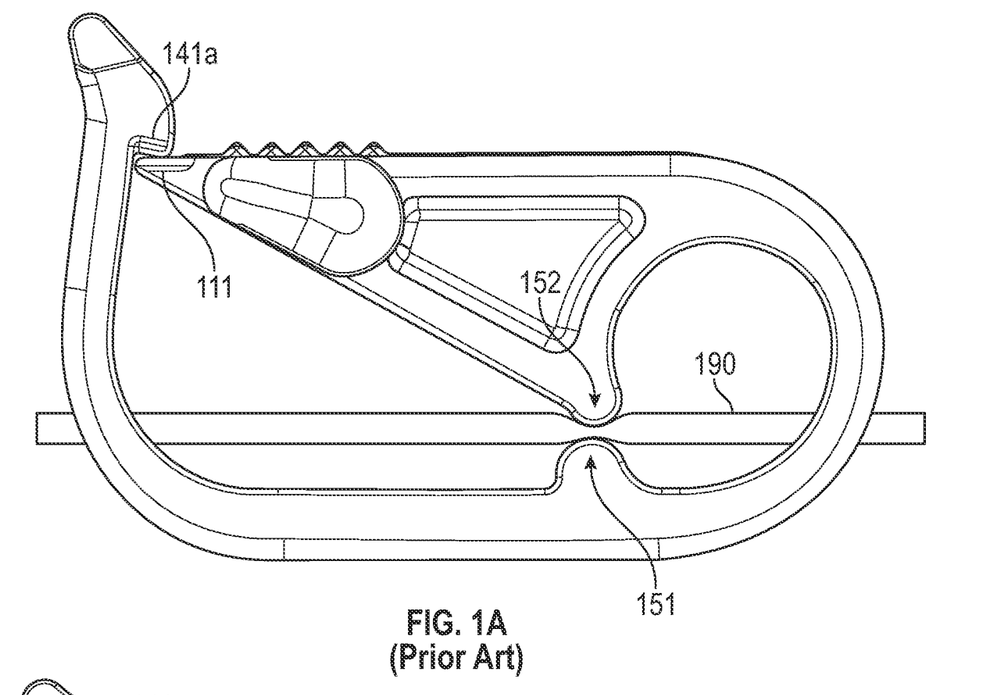
FIGS. 1A-1C illustrate a prior art pinch clamp including how the pinch clamp causes reflux when the pinch clamp is over-engaged.
Figure 1B:
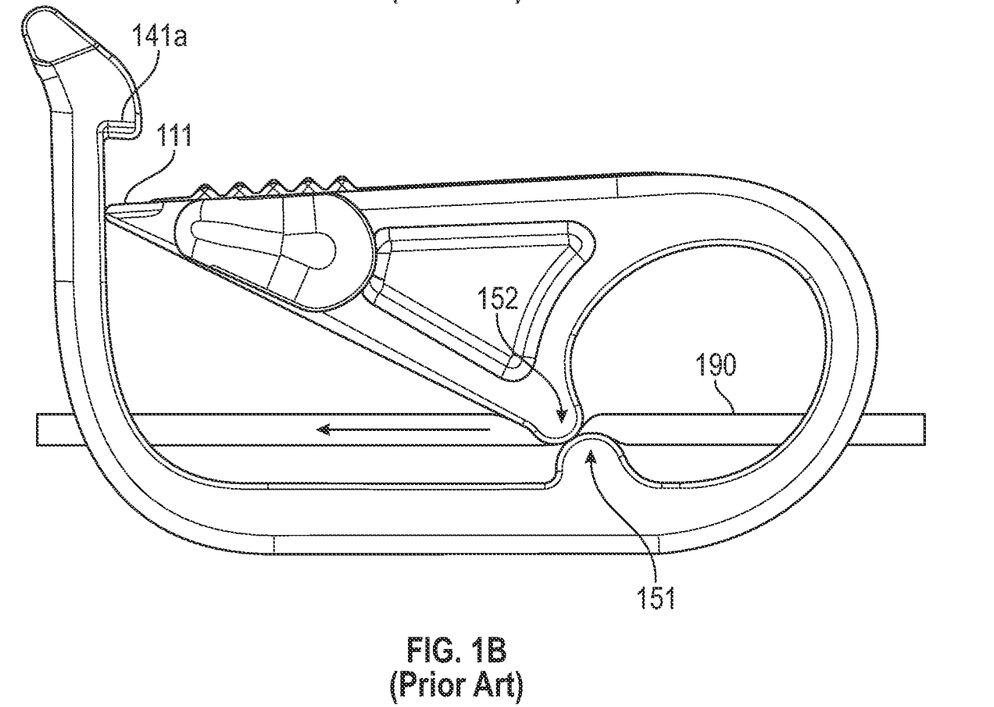
Figure 1C:
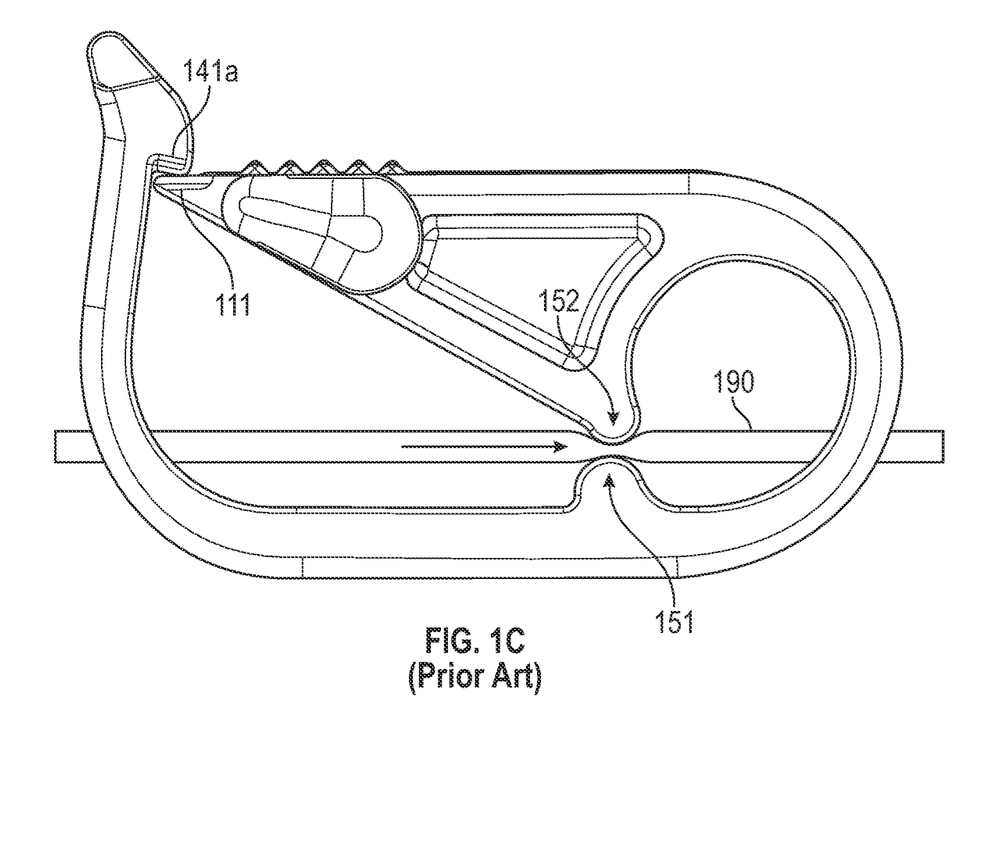

Many pinch clamp designs also enable over-engagement which may result in rebound. FIGS. 1A-1C illustrate an example of how rebound may occur when a pinch clamp 100 is over-engaged. Pinch clamp 100 includes an upper arm 110 that is connected to a lower arm 120 via a living hinge 130. A terminal portion 140 (where "terminal" represents that terminal portion 140 is towards the patient or distal end of tubing 190 relative to living hinge 130) extends upwardly from lower arm 120 opposite living hinge 130. An engaging structure 141 is formed at the upper end of terminal portion 140. Engaging structure 141 forms an engaging surface 141 that is oriented downwardly to enable the leading end 111 of upper arm 110 to be maintained below engaging surface 141 to thereby engage pinch clamp 100. In this engaged position, lower clamping surface 151 and upper clamping surface 152 are positioned with sufficient proximity to obstruct tubing 190 that extends through pinch clamp 100.

FIG. 1A illustrates pinch clamp 100 when in the engaged position. To move pinch clamp 100 into this engaged position, the clinician will typically squeeze upper and lower arms 110, 120 until leading end 111 of upper arm 110 drops below engaging surface 141. At that point, the biased terminal portion 140 will maintain leading end 111 beneath engaging surface 141. Difficulties arise, however, due to the ability of upper arm 110 to travel downwardly beyond what is necessary to reach the engaged position. For example, FIG. 1B illustrates that upper arm 110 has been forced downward so that leading end 111 has traveled substantially beyond engaging surface 141a. As a result, upper clamping surface 152 has contacted lower clamping surface 151 and traveled in a forward direction (i.e., towards terminal end 140) relative to lower clamping surface 151.

This forward movement of upper clamping surface 152 relative to lower clamping surface 151 results in "positive displacement" of the fluid within tubing 190 as represented by the arrow in FIG. 1B. In other words, the over-engagement of pinch clamp 100 will cause fluid within tubing 190 to flow into or at least towards the patient. Positive displacement is generally desirable. However, in this scenario, because the positive displacement is a result of over-engagement, a rebound will occur as represented in FIG. 1C. In FIG. 1C, it is assumed that the clinician is no longer squeezing pinch clamp 100 and therefore, upper arm 110 has pivoted upwardly back to the engaged position (i.e., until leading end 111 contacts engaging surface 141a). This upward movement of upper arm 110 relative to lower arm 120 will cause upper clamping surface 152 to also travel in an upward and somewhat backward direction. This upward and backward movement increases the internal volume of tubing 190 downstream from the "pinch point." (i.e., the point where lower clamping surface 151 and upper clamping surface 152 occlude tubing 190). As a result, fluid—likely including blood—will be sucked into the catheter of other device to which tubing 190 is coupled. The term rebound represents this transition from the over-engaged position depicted in FIG. 1B to the engaged position depicted in FIG. 1C.

The reflux that results from a pinch clamp rebound creates a number of problems. For example, the reflux of blood can increase the risk of occlusion (e.g., due to an intraluminal thrombus within the catheter) which may prevent fluids from being infused through the catheter or prevent blood from being withdrawn. Even if occlusion does not occur, the reflux can increase the risk of infection.

SUMMARY

The present disclosure relates generally to pinch clamps that are designed to provide positive displacement while also preventing rebound. As a result, the design of these pinch clamps minimizes the occurrence of reflux. In addition to preventing rebound, the design of the pinch clamps can prevent lateral disengagement, minimize the force required for engagement and enhance patient comfort.

To prevent rebound while providing positive displacement, the upper and lower clamping surfaces may be configured to form a pinch profile along which the tubing is compressed with the pinch point being formed at the distal end of the pinch profile. To further prevent rebound, the lower arm of the pinch clamp can include blocking ribs that interface with the upper clamping surface to prevent distal travelling of the pinch point even if the upper arm is forced into an over-engaged position.

In some embodiments, the present invention is implemented as a pinch clamp that includes an upper arm having a proximal end and a distal end and a lower arm having a proximal end and a distal end where the proximal end of the lower arm is coupled to the proximal end of the upper arm via a hinge. The pinch clamp also includes a terminal end that extends upwardly from the distal end of the lower arm. The terminal end includes an engaging structure that forms an engaging surface that interfaces with the distal end of the upper arm to retain the pinch clamp in an engaged position. An upper clamping surface is formed on the upper arm and has a proximal portion and a distal portion. Also, a lower clamping surface is formed on the lower arm and has a proximal portion and a distal portion. When the pinch clamp is in the engaged position, a distance between the distal portion of the upper clamping surface and the distal portion of the lower clamping surface is less than a distance between the proximal portion of the upper clamping surface and the proximal portion of the lower clamping surface.

In other embodiments, the present invention is implemented as a pinch clamp that includes an upper arm having a proximal end and a distal end and a lower arm having a proximal end and a distal end where the proximal end of the lower arm is coupled to the proximal end of the upper arm via a hinge. The pinch clamp also includes a terminal end that extends upwardly from the distal end of the lower arm. The terminal end includes an engaging structure that forms an engaging surface that interfaces with the distal end of the upper arm to retain the pinch clamp in an engaged position. An upper clamping surface is formed on the upper arm and has a proximal portion and a distal portion. Also, a lower clamping surface is formed on the lower arm and has a proximal portion and a distal portion. The pinch clamp further includes blocking ribs that are positioned on opposing sides of the lower arm and extend distally from the distal portion of the lower clamping surface.

In other embodiments, the present invention is implemented as a pinch clamp that includes an upper arm having a proximal end and a distal end and a lower arm having a proximal end and a distal end where the proximal end of the lower arm is coupled to the proximal end of the upper arm via a hinge. The pinch clamp also includes a terminal end that extends upwardly from the distal end of the lower arm. The terminal end includes an engaging structure that forms an engaging surface that interfaces with the distal end of the upper arm to retain the pinch clamp in an engaged position. An upper clamping surface is formed on the upper arm and has a flat proximal portion and a distal portion that protrudes downwardly from the flat proximal portion. A lower clamping surface is formed on the lower arm and is flat.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Pinch clamps that are configured in accordance with the present invention can provide positive displacement while also preventing rebound to thereby minimize the occurrence of reflux. By structuring the upper and lower clamping surfaces to provide a pinch profile, as opposed to a single pinch point, the pinch clamps of the present invention can cause positive displacement. Additionally, the upper and lower clamping surfaces can be configured to form the pinch point towards the distal end of the pinch profile. The positioning of the pinch point towards the distal end can minimize the likelihood of rebound if the pinch clamp is over-engaged. Alternatively or additionally, the pinch clamps can include blocking ribs that interface with the upper clamping surface to prevent distal travelling of the pinch point even if the upper arm is forced into an over-engaged position FIGS. 2A-2E provide various views of a pinch clamp 200 that is configured in accordance with embodiments of the present invention. Pinch clamp 200 includes an upper arm 210, a lower arm 220, a living hinge 230 that couples the proximal ends of upper and lower arms 210, 220 and a terminal end 240 that extends upwardly from the distal end of lower arm 220. Living hinge 230 and terminal end 240 form openings 230a and 240a respectively through which tubing (not shown) extends. An upper portion of terminal end 240 forms an engaging structure 241 having a downward facing engaging surface 241a. Upper arm 210 pivots relative to lower arm 220 to allow leading end 211 of upper arm 210 to be secured under engaging surface 241a to thereby maintain pinch clamp 200 in the engaged position. In some embodiments, leading end 211 may include a protruding portion 212 that extends outwardly from one side of upper arm 210. To enhance grip, upper arm 210 and lower arm 220 may include a series of ridges 213 and 222 respectively that span the width of the respective arm.

Figure 2A:
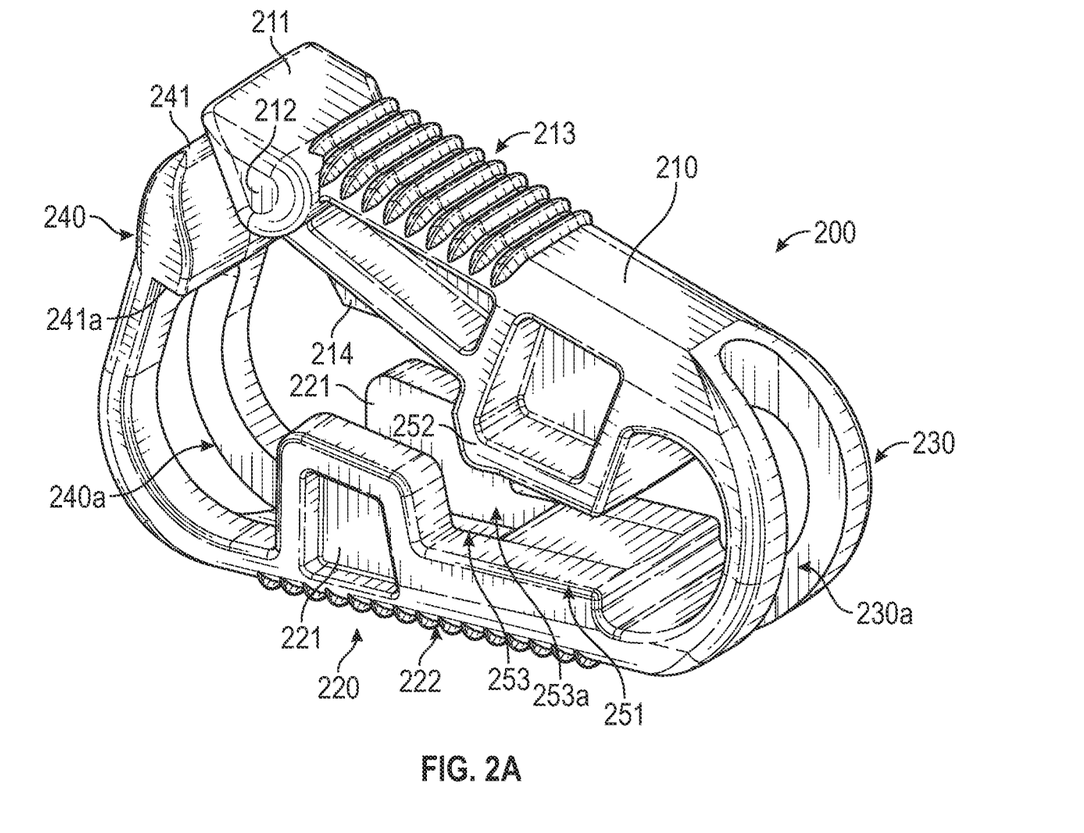
FIG. 2A provides a front perspective view of a pinch clamp configured in accordance with embodiments of the present invention.
Figure 2B:
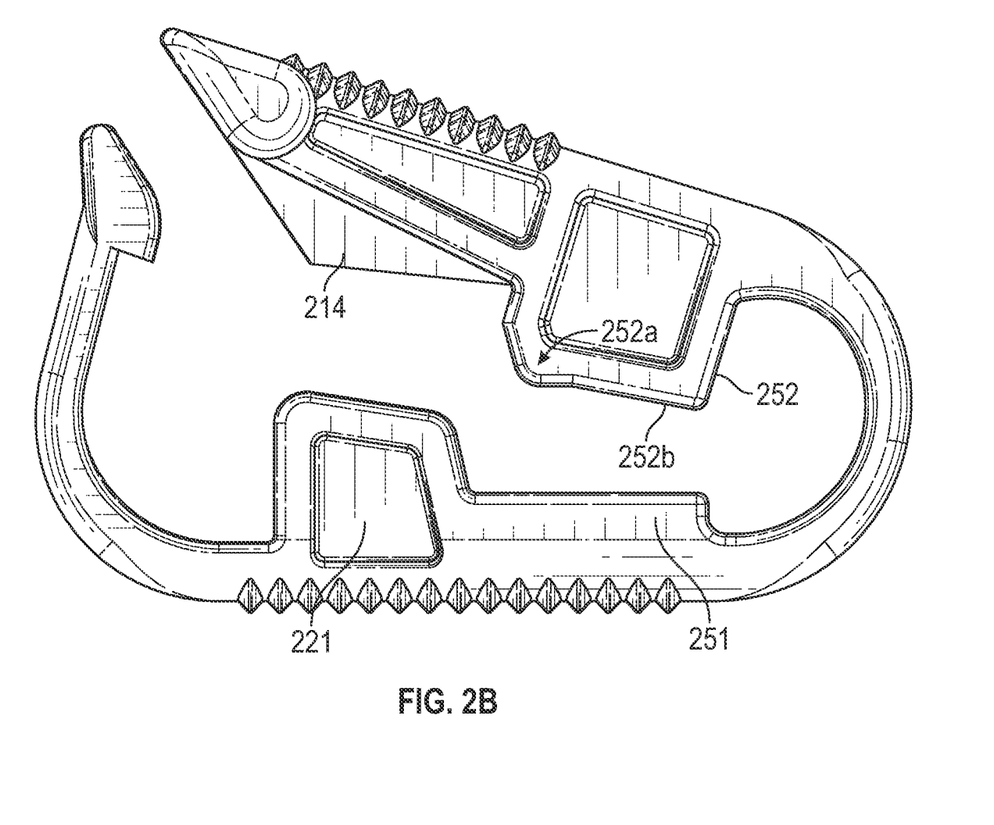
FIG. 2B provides a front view of the pinch clamp of FIG. 2A.
Figure 5:
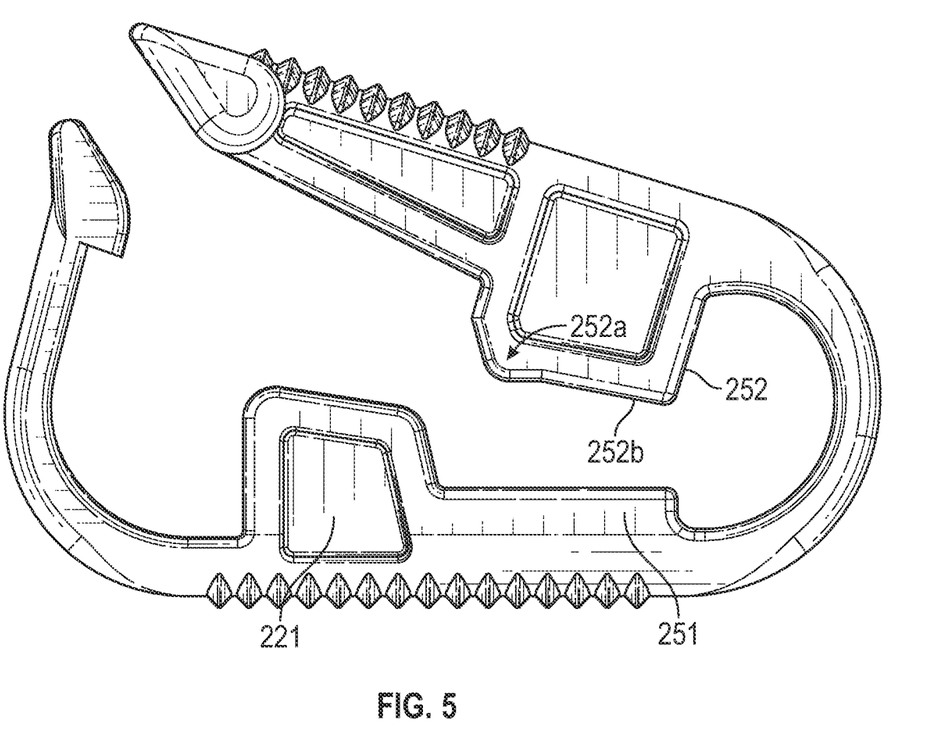
FIG. 5 illustrates a pinch clamp configured in accordance with another embodiment of the present invention.

To prevent lateral disengagement, lower arm 220 can include tabs 221 that extend upwardly from opposing sides of lower arm 220 to thereby form a gap between the tabs. Upper arm 210 can include a rib 214 that extends downwardly from the underside of upper arm 210 and that is configured to insert into the gap between tabs 221. The interface between rib 214 and tabs 221 will prevent upper arm 210 from moving laterally relative to lower arm 220 while in the engaged position thereby preventing leading end 211 from becoming laterally disengaged from engaging surface 241a. As is best seen in FIG. 2B, rib 214 and tabs 221 can be positioned towards terminal end 240. In addition to preventing lateral disengagement, tabs 221 also function to center the tubing between lower arm 210 and upper arm 220. In other embodiments, pinch clamp 200 may not include rib 214 as is shown in FIG. 5. In such embodiments, pinch clamp 200 can be disengaged by lateral movement but will still provide positive displacement and center the tubing.

Figure 2C:
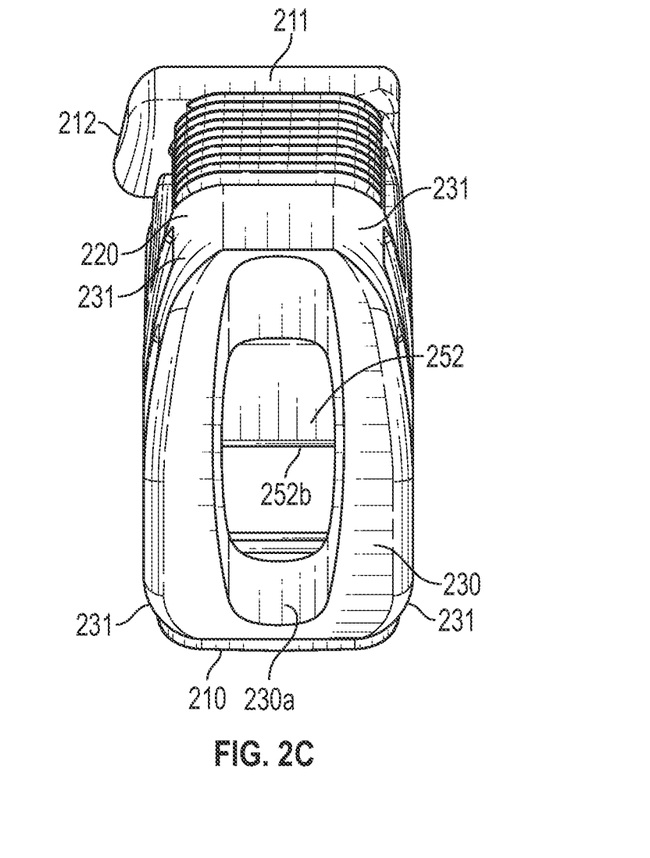
FIG. 2C provides a side view of the pinch clamp of FIG. 2A.

As is best shown in FIG. 2B, pinch clamp 200 can be configured so that, when lower arm 220 is horizontal and pinch clamp 220 is in the disengaged position, upper arm 210 will be oriented at an upward angle. Also, as best shown in FIG. 2C, the outer edges 231 of upper arm 210 and lower arm 220 are rounded to eliminate sharp edges and thereby enhance patient comfort.

Upper arm 210 forms an upper clamping surface 252 that is positioned proximal to and extends downwardly beyond rib 214. In some embodiments, including the embodiment depicted in FIGS. 2A-2E, upper clamping surface 252 includes a generally flat proximal portion 252b and a protruding distal portion 252a. In other embodiments, upper clamping surface 252 may not include protruding distal portion 252a such that upper clamping surface 252 is generally flat from its proximal end to its distal end. Lower arm 220 forms a lower clamping surface 251 that is generally flat. Blocking ribs 253 extend distally beyond a distal end of lower clamping surface 251 along opposing sides of lower arm 220. A gap 253a is thereby formed between blocking ribs 253 distal to lower clamping surface 251. In some embodiments, tabs 221 comprise a raised extension of blocking ribs 253.

Figure 2D:
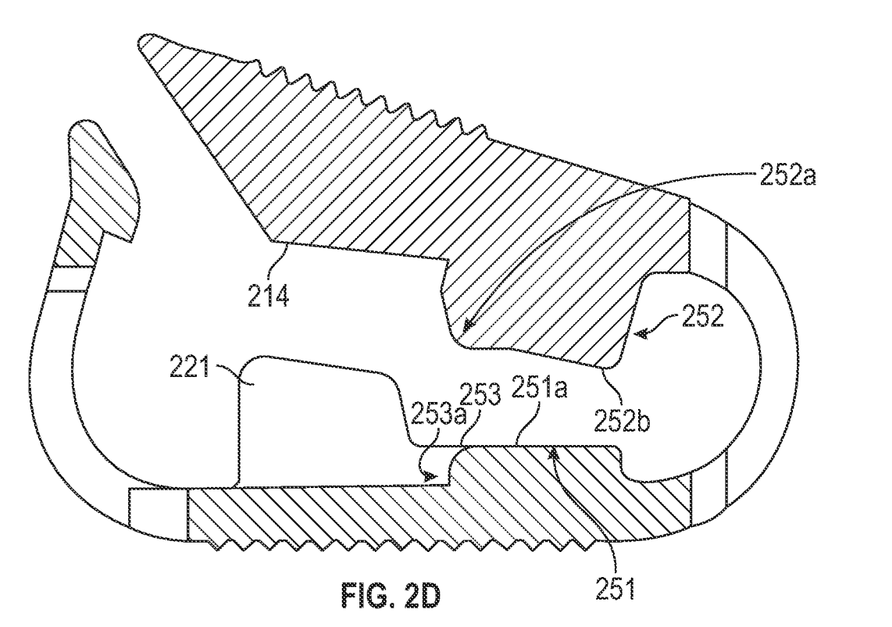
FIG. 2D provides a cross-sectional front view of the pinch clamp of FIG. 2A when in the disengaged position.
Figure 2E:
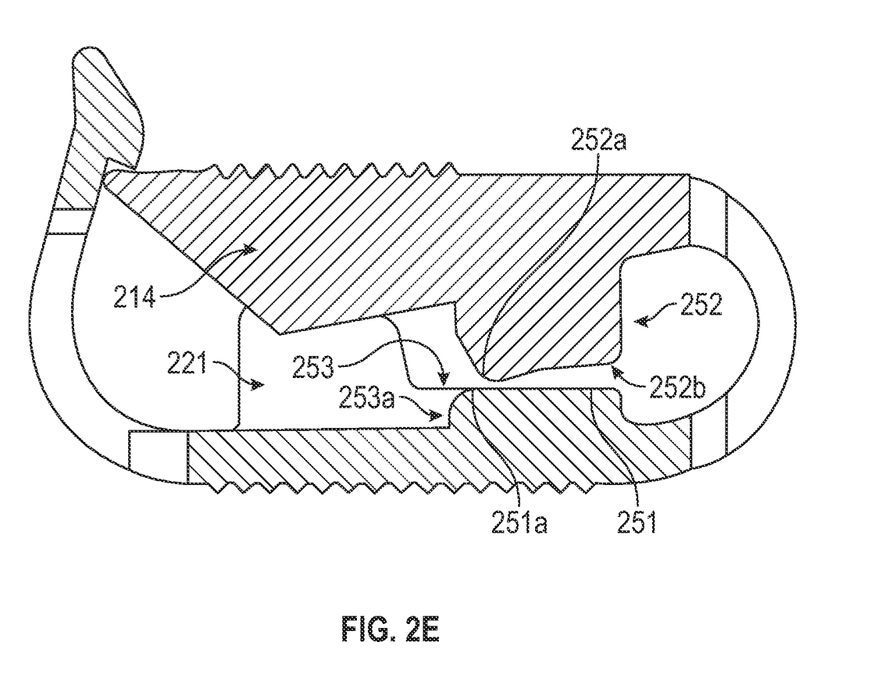
FIG. 2E provides a cross-sectional front view of the pinch clamp of FIG. 2A when in the engaged position.

Upper clamping surface 252 and lower clamping surface 251 are both elongated to thereby create a pinch profile when pinch clamp 200 is in the engaged position. With reference to FIGS. 2D and 2E, upper clamping surface 252 can be configured so that it is angled upwardly in a distal direction relative to lower clamping surface 251 when pinch clamp is in the disengaged position. Then, once pinch clamp 200 is transitioned into the engaged position, upper clamping surface 252 pivots into a downward orientation relative to lower clamping surface 251. As part of this transition, proximal portion 252b will first contact and compress the tubing towards a proximal end of lower clamping surface 251. This compression of the tubing will cause positive displacement. As pinch clamp 200 transitions fully into the engaged position and due to the downwardly angled orientation of upper clamping surface 252, distal portion 252a will contact, compress and occlude the tubing (i.e., create the pinch point) towards a distal end of lower clamping surface 251. Accordingly, the pinch profile consists of compression of the tubing towards the proximal end of clamping surfaces 251/252 and occlusion of the tubing at the distal end of clamping surfaces 251/252.

The force required to occlude the tubing is minimized by providing protruding distal portion 252a. More specifically, protruding distal portion 252a minimizes the length of the tubing that is occluded thereby minimizing the squeezing force required to reach the engaged position. In contrast, if upper clamping surface 252 is flat, a greater length of tubing would be compressed and occluded thereby increasing the squeezing force required to reach the engaged position.

Again with reference to FIG. 2E, due to the positioning of blocking ribs 253, if an over-engaging force is applied to pinch clamp 200, upper clamping surface 252 will be blocked from travelling in a downward direction relative to lower clamping surface 251. In other words, blocking ribs 253 will prevent the pinch point from travelling in a distal direction thereby preventing rebound once the over-engaging force is removed. The generally flat orientation of lower clamping surface 251 and blocking ribs 253 combined with the downwardly angled orientation of upper clamping surface 252 will also convert the over-engaging force on upper arm 220 into a pivoting force around distal portion 252a. This pivoting force will minimize the likelihood that upper clamping surface 252 will slide in a distal direction relative to lower clamping surface 251.

Figure 3:
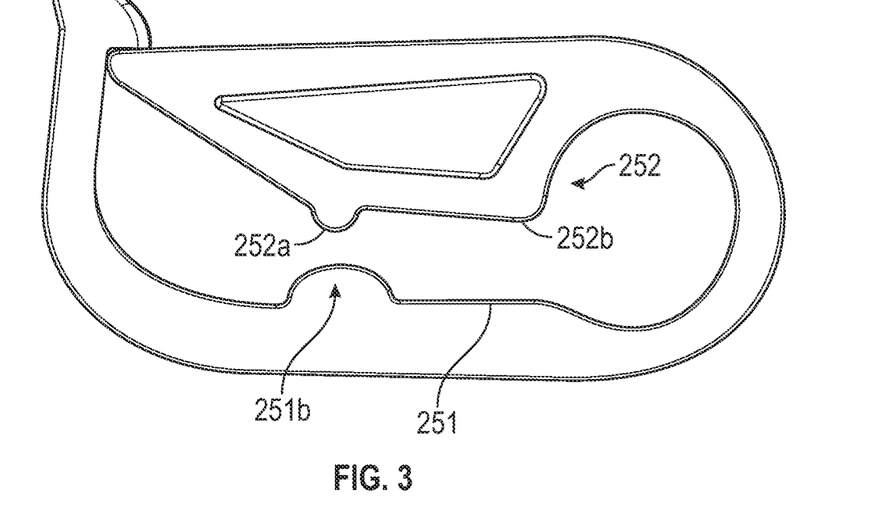
FIG. 3 illustrates a pinch clamp configured in accordance with another embodiment of the present invention.

FIG. 3 illustrates an alternate configuration of lower clamping surface 251 and upper clamping surface 252 that also provides a pinch profile. In this embodiment, upper clamping surface 252 includes a generally flat proximal portion 252b and a protruding distal portion 252a similar to what was described above. However, lower clamping surface 251 also includes a protruding distal portion 251b that generally aligns with distal portion 252a but that is elongated relative to distal portion 252a. In this configuration, the generally flat proximal portions of upper and lower clamping surfaces 252/251 will compress the tubing while distal portions 252a/251a will form the pinch point.

Figure 4:
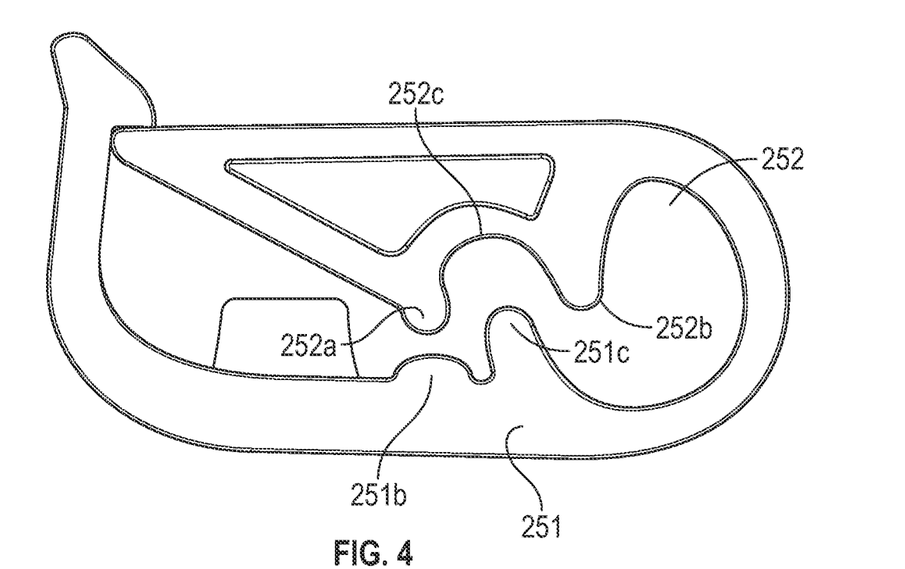
FIG. 4 illustrates a pinch clamp configured in accordance with another embodiment of the present invention.

FIG. 4 illustrates another alternate configuration of lower clamping surface 251 and upper clamping surface 252 that also provides a pinch profile. In this embodiment, lower clamping surface 251 is not flat, but includes a protruding proximal portion 251b in addition to protruding distal portion 251a. Proximal portion 251b protrudes upwardly farther than distal portion 251a. Upper clamping surface 252 includes protruding distal portion 252a as well as a protruding proximal portion 252b. A recessed portion 252c is formed between distal portion 252a and proximal portion 252b and has a curved shape that corresponds to the curved shape of proximal portion 251b. Proximal portion 251b inserts into recessed portion 252c which in turn can prevent over-engagement of the pinch clamp.

As shown in FIG. 4, when in the engaged position, a generally constant spacing is formed between proximal portion 251b and recessed portion 252c and between proximal portion 251b and proximal portion 252b. This constant spacing forms a channel in which the tubing will be compressed but not occluded. In contrast, in the engaged position, the spacing between distal portion 252a and distal portion 251a is less than the constant spacing between the other portions so that a pinch point is formed between distal portions 252a/251a.

In the embodiments shown in FIGS. 3 and 4, the elongated upper and lower clamping surfaces will provide positive displacement and will also prevent rebound. Rebound is prevented due to the pinch profile which positions the pinch point at the distal end of the clamping surfaces.

In summary, the pinch clamps of the present invention include upper and lower clamping surfaces that are configured to provide a pinch profile. This pinch profile provides positive displacement by compressing the tubing towards the proximal end of the clamping surfaces and prevents rebound by positioning the pinch point towards the distal end of the clamping surfaces.

We claim:

1. A pinch clamp to clamp a medical tubing, comprising:
a lower arm comprising a lower clamping surface, wherein the lower clamping surface comprises an upwardly protruding proximal portion and an upwardly protruding distal portion, wherein the upwardly protruding proximal portion protrudes upwardly further than the upwardly protruding distal portion;
an upper arm comprising an upper clamping surface, wherein the upper clamping surface comprises a downwardly protruding proximal portion, a downwardly protruding distal portion, and a recessed portion between the downwardly protruding proximal portion and the downwardly protruding distal portion, wherein the upwardly protruding proximal portion is configured to insert into the recessed portion when the pinch clamp is in an engaged position, wherein the upwardly protruding distal portion is configured to be aligned with the downwardly protruding distal portion when the pinch clamp is in the engaged position; and
a hinge disposed between the lower arm and the upper arm,
wherein a space between the downwardly protruding distal portion and the upwardly protruding distal portion is less than a space between the recessed portion and the upwardly protruding proximal portion when the pinch clamp is in the engaged position.

2. The pinch clamp of claim 1, further comprising a terminal end extending upwardly from a distal end of the lower arm, wherein the terminal end forms an engaging structure having a downward facing engaging surface, wherein the upper arm is configured to pivot relative to the lower arm and to be secured under the engaging surface when the pinch clamp is in the engaged position.

3. The pinch clamp of claim 1, further comprising a channel disposed between the upper clamping surface and the lower clamping surface.

\* \* \* \* \*